United States Patent [19]

Sullivan et al.

[11] Patent Number: 4,654,504
[45] Date of Patent: Mar. 31, 1987

[54] WATER-COOLED GAS DISCHARGE DETECTOR

[75] Inventors: James J. Sullivan, Newark, Del.; Bruce D. Quimby, Landenberg, Pa.

[73] Assignee: Hewlett-Packard Company, Palo Alto, Calif.

[21] Appl. No.: 556,527

[22] Filed: Nov. 30, 1983

[51] Int. Cl.⁴ .............................................. B23K 9/00
[52] U.S. Cl. ...................... 219/121 PM; 219/121 PN; 356/316
[58] Field of Search ................ 219/121 PM, 121 PN, 219/121 PQ, 121 PR, 137.62; 356/316; 204/192 C, 192 P, 192 R, 298; 250/372

[56] References Cited

U.S. PATENT DOCUMENTS

| 3,484,650 | 12/1969 | Rendina | 356/316 X |
| 3,492,074 | 1/1970 | Rendina | 356/316 |
| 3,626,234 | 12/1971 | Grimm | 356/316 X |
| 3,635,561 | 1/1972 | Bordonali et al. | 356/316 X |
| 4,322,165 | 3/1982 | Ellebracht et al. | 356/316 |
| 4,394,237 | 7/1983 | Donnelly et al. | 204/192 E |

OTHER PUBLICATIONS

McCormack, et al; "Sensitive Selective Gas Chromatography Detector Based on Emission Spectrometry of Organic Compounds"; *Analytical Chemistry*; vol. 30; pp. 1470–1476.

*Primary Examiner*—E. A. Goldberg
*Assistant Examiner*—M. Lateef
*Attorney, Agent, or Firm*—Donald N. Timbie

[57] ABSTRACT

The radio frequency powered gas discharge tube of an atomic emission detector is cooled with a flow of liquid, and means are provided for grounding points in the flow that are on opposite sides of the radio frequency field so as to reduce the amount of radio frequency energy escaping from the discharge tube in the liquid.

7 Claims, 2 Drawing Figures

WATER-COOLED GAS DISCHARGE DETECTOR

BACKGROUND OF THE INVENTION

This invention relates to improvements in a gas chromatographic detector having an RF powered plasma giving off light that is analyzed by emission spectroscopy as reported by McCormack, Tong and Cooke in *Analytical Chemistry*, 1965, 37, 1470. In their detector, gas containing the chemical compounds to be analayzed is passed through a discharge contained within a tube mounted within the resonant microwave cavity that, because of cost considerations, is powered by the magnetron used in microwave ovens for the home. The microwave powered discharge in the discharge tube breaks the molecules of the gas into atoms. The discharge excites the atoms so that characteristic spectral emission of the atoms is given off.

Inasmuch as the problem of tailing has generally been the fault of the column employed and not the fault of the detector, it has been presumed that the tailing usually present when an automatic emission detector was used was also due to the column. We have discovered, however, that an error of as much as 5% has been due to tailing caused by the detector itself and that this is due to the fact that the inner walls of the discharge tube run at a very high temperature. Furthermore, the high temperature causes rapid degradation of the discharge tube so that it must be replaced often. Because of its location, replacement of a discharge tube can take a few hours during which the detector can be out of service. Whereas these problems can be partially overcome by reducing the radio frequency power employed, this degrades the sensitivity of the detector.

BRIEF SUMMARY OF THE INVENTION

In accordance with this invention, the inside surface of the discharge tube is cooled by using means for bringing a flow of coolant into thermal communication with the outside surface. This reduces the erosion of the inner surface so as to permit the attainment of a satisfactory discharge tube life along with a significant increase in radio frequency power and detector sensitivity.

Whereas it seemed that air could be used as a coolant, it was found that its thermal impedance was so different from that of the materials from which the discharge tube is generally made that the rate of flow of heat into the air was too low to obtain sufficient cooling, even though the flow of air was raised to a high level.

It also was found that coolant liquids such as certain freons, oils, hydrocarbons and silicones can be used, but it turned out that they could be carbonized if momentarily overheated, for instance, if the flow is momentarily interrupted, so as to produce a carbon coating that tends to shield the interior of the tube from the microwave energy and reduce the sensitivity of the detector. Furthermore, the formation of any carbon increases the rate of formation of additional carbon so that the detector soon becomes inoperative. Then, too, many of these coolant materials are so flammable or toxic as to make their use undesirable. None of these problems occur when water is used.

At first, it seemed that water could be used as a coolant, but unfortunately the frequency used in magnetrons for home oven use is understandably selected to be one that is absorbed by water. Interestingly enough, however, it was found that, even though the amount of water in the cavity was reduced to the point that it absorbed only an insignificant amount of power, no discharge occurred. It was then discovered that, even with purified water, the microwave conductivity was high enough for the liquid flow path to have some of the characteristics of an electrical conductor. When water in the flow path was contained within a dielectric tube, the combination served as an effective conduit to transmit microwave power away from the cavity and to radiate it. In order to prevent this from occurring, a detector constructed in accordance with this invention has means for connecting the flow path to electrical ground, usually on the walls of the cavity. The location and geometry of this connection must be sufficiently extensive to substantially reduce the microwave energy flow before it reaches a portion of the liquid flow path that is unshielded.

DETAILED DESCRIPTION OF THE INVENTION

Figure 1:
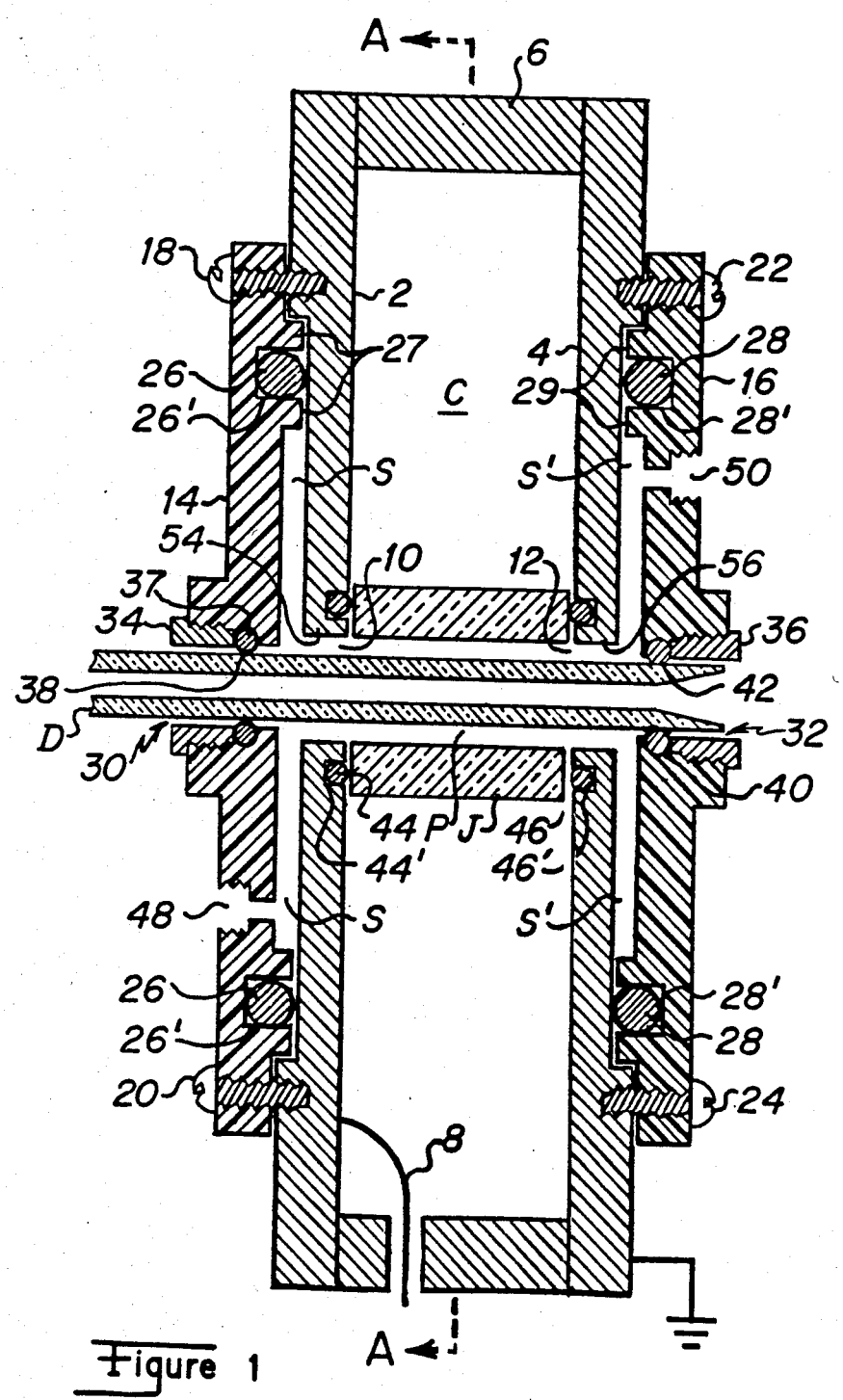
FIG. 1 is an end view of the axis of an atomic emission detector.
Figure 2:
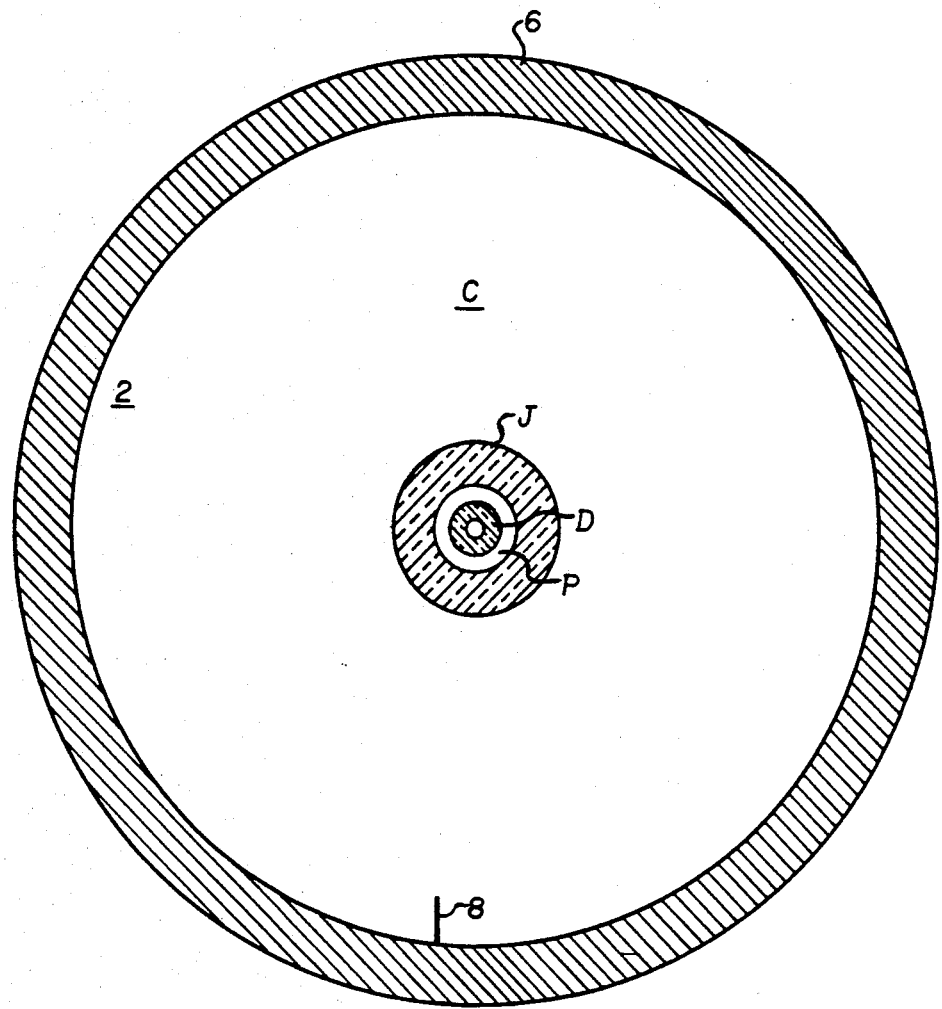
FIG. 2 is a cross-section AA of FIG. 1.

The particular embodiment of an atomic emission detector shown in the drawings is comprised of a metal cavity C formed with parallel planar circular disks 2 and 4 that are sealed all around their outer edges by a metal strip 6. A probe 8 introduces radio frequency energy into the cavity C. The disks 2 and 4 respectively have circular apertures 10 and 12 that are concentric therewith and which have a radius larger than the outer radius of a discharge tube D inserted therethrough. Circular metal or plastic discharge tube support members 14 and 16, herein shown as being plastic, are respectively attached to the outer sides of the disks 2 and 4 by screws 18, 20 and 22, 24. Depending on the geometry, parts 14 and 16 may have to be metal, in accordance with the principal of having a sufficiently extensive grounding of the flow path. A rubber O-ring 26 that is contained in a concentric annular groove 26' on the inside of the circular member 14 forms a hermetic seal between that member and the outside of the disk 2 when the screws 18 and 20 are tightened sufficiently; and a rubber O-ring 28 that is contained in a concentric annular groove 28' on the inside of the circular member 16 forms a hermetic seal between that member and the outside of the disk 4 when the screws 22 and 24 are tightened sufficiently. The inner edges 27 of the annular groove 26' space the central portion of the inner surface of the support member 14 from the outside of the wall 2 of the cavity C so as to form a cylindrical space S therebetween; and the inner edges 29 of the annular groove 28' space the central portion of the inner surface of the support member 16 from the outside of the wall 4 of the cavity C so as to form a cylindrical space S' therebetween.

The circular discharge tube support members 14 and 16 are provided with circular central apertures 30 and 32 respectively that are coaxially aligned with the apertures 10 and 12 and that are just slightly larger than the discharge tube D that is coaxially mounted within all of the apertures 30, 10, 12 and 32. The discharge tube D is made of a refractory material of low microwave dissipation factor and high chemical inertness such as fused silica, boron nitride or crystalline alumina (sapphire) and is inserted through annular nuts 34 and 36 that are respectively screwed into threads on the insides of the apertures 30 and 32. A seal is provided between the outside of the discharge tube D and an annular shoulder 37 in the aperture 30 by pressing a rubber O-ring 38 between the shoulder 37 and the end of the annular nut 34. Similarly, a seal is provided between the outside of the discharge tube D and an annular shoulder 40 in the aperture 32 by pressing a rubber O-ring 42 between the shoulder 40 and the end of the annular nut 36.

An annular water jacket J that is made of quartz, polystyrene or any other low dielectric constant, low dissipation factor material is mounted concentrically with the discharge tube D and has an inner radius that is greater than the outer radius of the discharge tube D so as to form an annular passageway P therebetween. The radial thckness of the passageway P is preferably as small as possible but large enough to permit sufficient flow to prevent boiling of the coolant. If the thickness is too large, the microwave tuning of the cavity is shifted and may be dependent on the temperature of the cooling liquid. Also, microwave power is dissipated in the liquid, so it is advantageous to keep the volume of liquid contained within the cavity to a minimum. The passageway P is sealed from the inside of the cavity C by rubber O-rings 44 and 46 that are respectively embedded in annular grooves 44' and 46' that are concentric with the discharge tube D and of such radius that the O-rings 44 and 46 bear up against the opposite ends of the annular water jacket J. An aperture 48 through the support member 14 communicates with the outer part of the annular space S; and an aperture 50 through the support member 16 that is diametrically opposed to the aperture 48 communicates with the outer part of the annular space S'. The aperture 48, the cylindrical space S and the aperture 10 at the center of the disk 2 form a path via which coolant liquid may flow into one end of the passageway P; and the cylindrical aperture 50, the annular space S' and the aperture 12 at the center of the disk 4 form a path via which coolant liquid may flow out of the passageway P.

In accordance with this invention, points along the paths referred to must be grounded so as to prevent the paths from acting as an antenna radiating microwave power outside the cavity C that is required for the formation of the gas discharge within the discharge tube D. In this particular embodiment, the grounding is effected by the contact of the coolant liquid with the grounded cavity C at the inner surfaces 54 and 56 of the apertures 10 and 12 respectively and with the outside portion of the walls 2 and 4 of the cavity C that form sides of the circular spaces S and S'. Good results have also been attained by grounding the paths at points farther away from the ends of the passageway P, but it is preferable to locate the ground points as near to the end of the passageway P as possible so as to reduce the length of the gas discharge in the discharge tube D and therefore reduce tailing.

In the embodiment of the invention shown herein, the paths through which the coolant liquid flows into and out of the annular passageway P are on opposite sides of the cavity C, but in embodiments not shown, good results can be obtained with a design in which both paths are on the same side of the cavity C.

Provision is made for some of the light emitted within the discharge tube to radiate out the right-hand opening. This light is separated into various wavelength regions and detected in a way known to those skilled in the art.

It will be apparent to those skilled in the art that cavities having a different shape from the cylindrical one shown could be used, e.g., a cavity with a re-entrant section, and that the structure of the means for bringing the coolant into thermal communication with the discharge tube could be considerably different.

What is claimed is:

1. In a gas discharge detector having a discharge tube through which gases including those to be analyzed are made to pass and in which said discharge tube is immersed in a radio frequency field within a cavity defined by walls, the combination of channel means in which a flow of liquid may be brought into thermal communication with at least a portion of the exterior of said discharge tube that is within said cavity, means defining a path through which liquid may be made to flow from a point outside of said cavity to said channel means, means defining a path through which liquid may be made to flow from said channel means to a path outside of said cavity, and means for grounding liquid in said paths so as to reduce the amount of radio frequency energy that is conveyed by the liquid in said paths to points outside of said cavity.

2. A gas discharge detector as set forth in claim 1 wherein said means for grounding liquid in said paths is a construction in which the wall defining the cavity are part of said channel means so that the liquid, when present, contacts said walls.

3. In a gas discharge detector having a discharge tube in a cavity that is energized with microwaves of a frequency such that the energy is readily absorbed by water, means for cooling said discharge tube, comprising a jacket defining a passageway through which water may be brought into thermal communication with at least a portion of the exterior of said discharge tube that is within said cavity, means defining paths lying outside said cavity whereby water may be conducted to and from said jacket, and means for electrically connecting water, when present in said paths to said cavity whereby the amount of microwave energy radiated through said paths is reduced.

4. A gas discharge detector as set forth in claim 3 wherein said jacket is a tube having an internal diameter greater than the external diameter of said discharge tube and mounted so as to provide a passageway around the discharge tube.

5. A gas discharge detector as set forth in claim 3 wherein said means for electrically connecting water when present in said paths to said cavity makes the connection to the water at the point where it enters and leaves the cavity.

6. A gas discharge detector, comprising
a cavity in which a radio frequency field may be established,
a discharge tube extending through said cavity,
a cooling jacket surrounding said discharge tube and spaced therefrom, and
means for electrically grounding any liquid that may be passed between said discharge tube and said cooling jacket at opposite ends of said discharge tube and cooling jacket so as to reduce the amount of radio frequency energy that is radiated outside of said cavity.

7. A method of cooling the discharge tube that lies within a radio frequency field produced within a cavity of a gas discharge detector, comprising causing a flow of water to pass through the radio frequency field in contact with at least a portion of the discharge tube, and electrically grounding the flow of water at both ends of the discharge tube.

* * * * *